United States Patent
Chan

(10) Patent No.: US 7,211,047 B2
(45) Date of Patent: May 1, 2007

(54) BLOOD PRESSURE MONITOR

(75) Inventor: Raymond Chan, Hunghom (HK)

(73) Assignee: IDT Technology Limited, Hunghom, Kowloon (HK)

( * ) Notice: Subject to any disclaimer, the term of this patent is extended or adjusted under 35 U.S.C. 154(b) by 0 days.

(21) Appl. No.: 11/108,695

(22) Filed: Apr. 19, 2005

(65) Prior Publication Data

US 2006/0235311 A1    Oct. 19, 2006

(51) Int. Cl.
*A61B 5/02* (2006.01)

(52) U.S. Cl. ..................................... 600/485
(58) Field of Classification Search ............. None
See application file for complete search history.

(56) References Cited

U.S. PATENT DOCUMENTS

| | | | |
|---|---|---|---|
| 4,510,942 A * | 4/1985 | Miyamae et al. ........... | 600/493 |
| 4,558,707 A | 12/1985 | Miyamae et al. | |
| 4,690,151 A * | 9/1987 | Utsunomiya et al. ....... | 600/495 |
| 4,944,305 A | 7/1990 | Takatsu et al. | |
| 5,339,821 A | 8/1994 | Fujimoto | |
| 5,697,376 A * | 12/1997 | Nomura et al. ............. | 600/300 |
| 5,868,135 A * | 2/1999 | Kaufman et al. ........... | 600/300 |
| 6,402,691 B1 | 6/2002 | Peddicord et al. | |
| 6,416,471 B1 * | 7/2002 | Kumar et al. ............... | 600/300 |
| 6,524,240 B1 * | 2/2003 | Thede ......................... | 600/300 |
| 2003/0060721 A1 | 3/2003 | Nakazawa et al. | |
| 2004/0116815 A1 | 6/2004 | Yang et al. | |
| 2006/0111637 A1 * | 5/2006 | Jacober et al. ............. | 600/490 |

FOREIGN PATENT DOCUMENTS

DE          43 34 273          4/1995

* cited by examiner

*Primary Examiner*—Charles A. Marmor, II
*Assistant Examiner*—Patricia C Mallari
(74) *Attorney, Agent, or Firm*—Leydig, Voit & Mayer, Ltd.

(57) ABSTRACT

A portable blood pressure measuring device comprises a casing, a pressure sensor sensing oscillations in pressure from a cuff attached to a user, and a microprocessor for determining blood pressure based on the oscillations in pressure sensed by the pressure sensor. A signal converter provided in the casing converts data from the pressure sensor into data for the microprocessor. A voice processor provided in the casing receives data from the microprocessor and generates a voice signal indicative of the blood pressure sensed by the pressure sensor.

5 Claims, 4 Drawing Sheets

Reference material:1999 World Health Organization-International Society of Hypertension Guidelines for the management of hypertension, Journal of Hypertension, 1999, 17(2): 151-183.

BLOOD PRESSURE MONITOR

The present invention relates to a blood pressure monitor or measuring device.

BACKGROUND OF THE INVENTION

More particularly, but not exclusively, the invention is concerned with a portable blood pressure measuring device that is for use at home.

Traditional home-use automatic blood pressure monitors display blood pressure readings on an LCD panel. Such panels can be difficult to read under dim or strong lighting conditions. Furthermore, most blood pressure monitors of this type do not have backlighting so the user may have difficulty in reading the readout in dark environments, such as at night time.

After using a blood pressure monitor to determine one's blood pressure, users usually compare their readings to the classification published by the World Health Organisation and International Society of Hypertension. Such published materials are often included in the handbook provided with domestic blood pressure monitors.

Most users of home blood pressure monitors are elderly and therefore it might not be easy for them to remember past systolic and diastolic readings or classifications, or indeed to compare measured readings with those which appear in the user manual, often in fine print.

In order to obtain accurate blood pressure measurements, the user must raise his or her arm to heart level, and then remain still without speaking as would be the case when having their blood pressure taken by a doctor.

OBJECTS OF THE INVENTION

It is an object of the present invention to overcome or substantially ameliorate one or more of the above problems by providing an improved portable blood pressure measuring device.

SUMMARY OF THE INVENTION

According to the invention, there is provided a portable blood pressure measuring device, comprising a casing, a pressure sensor adapted to sense oscillations in pressure from a cuff attached to a user, and a microprocessor provided in the casing for determining blood pressure based on said oscillations in pressure sensed by the pressure sensor. There is a signal converter provided in the casing for operatively converting data from the pressure sensor into data for processing by the microprocessor. Also included is a voice processor provided in the casing for operatively receiving data from the microprocessor and then generating a voice signal indicative of blood pressure determined by the microprocessor.

Preferably, the voice processor includes a sound generator for operatively reproducing said voice signal generated by the voice processor.

More preferably, the sound generator comprises a speaker provided in the casing.

It is preferred that the voice processor is controlled by the microprocessor to generate a said voice signal each time blood pressure is determined.

In a specific construction, the measuring device includes a pump provided in the casing and a valve connected between the pump and the pressure sensor, the pump and valve being operatively activated by the microprocessor.

Preferably, the measuring device includes a display panel on the casing for displaying data from the microprocessor.

Preferably, the measuring device includes user input keys on the casing for providing user-input to the microprocessor, including at least two user keys for different users.

In a preferred embodiment, the measuring device includes memory means storing a user guide to blood pressure measurement, and the voice processor is controlled by the microprocessor to generate voice guidance based on said user guide for a user to prepare for blood pressure measurement.

In a preferred embodiment, the measuring device includes memory means storing a set of blood pressure classifications, and the voice processor is controlled by the microprocessor to generate a voice signal indicative of a suitable classification selected from the classifications, which corresponds to blood pressure determined by the microprocessor.

In a preferred embodiment, the measuring device includes time-keeping means associated with the microprocessor for time keeping comprising providing the time and a daily alarm.

More preferably, the measuring device includes memory means connected to the microprocessor for operatively storing values of blood pressure determined by the microprocessor against time of measurement, wherein the microprocessor is programmed to determine an optimal time of the day for blood pressure measurement, based on the blood pressure values against time stored in the memory means, and to indicate the optimal time.

Further more preferably, the time-keeping means is controlled by the microprocessor to provide a daily alarm at the optimal time.

Yet further more preferably, the voice processor is controlled by the microprocessor to generate a voice signal at the optimal time according to the time-keeping means, acting as the daily alarm.

More preferably, the microprocessor is programmed to identify, from the blood pressure values against time stored in the memory means, occurrence of borderline or high blood pressure twice within a predetermined period and then to provide an alert signal.

Further more preferably, the microprocessor is adapted to provide said alert signal by controlling the voice processor to generate a voice signal recommending medical attention.

BRIEF DESCRIPTION OF DRAWINGS

The invention will now be more particularly described, by way of example only, with reference to the accompanying drawings, in which.

DETAILED DESCRIPTION OF PREFERRED EMBODIMENT

Figure 1:
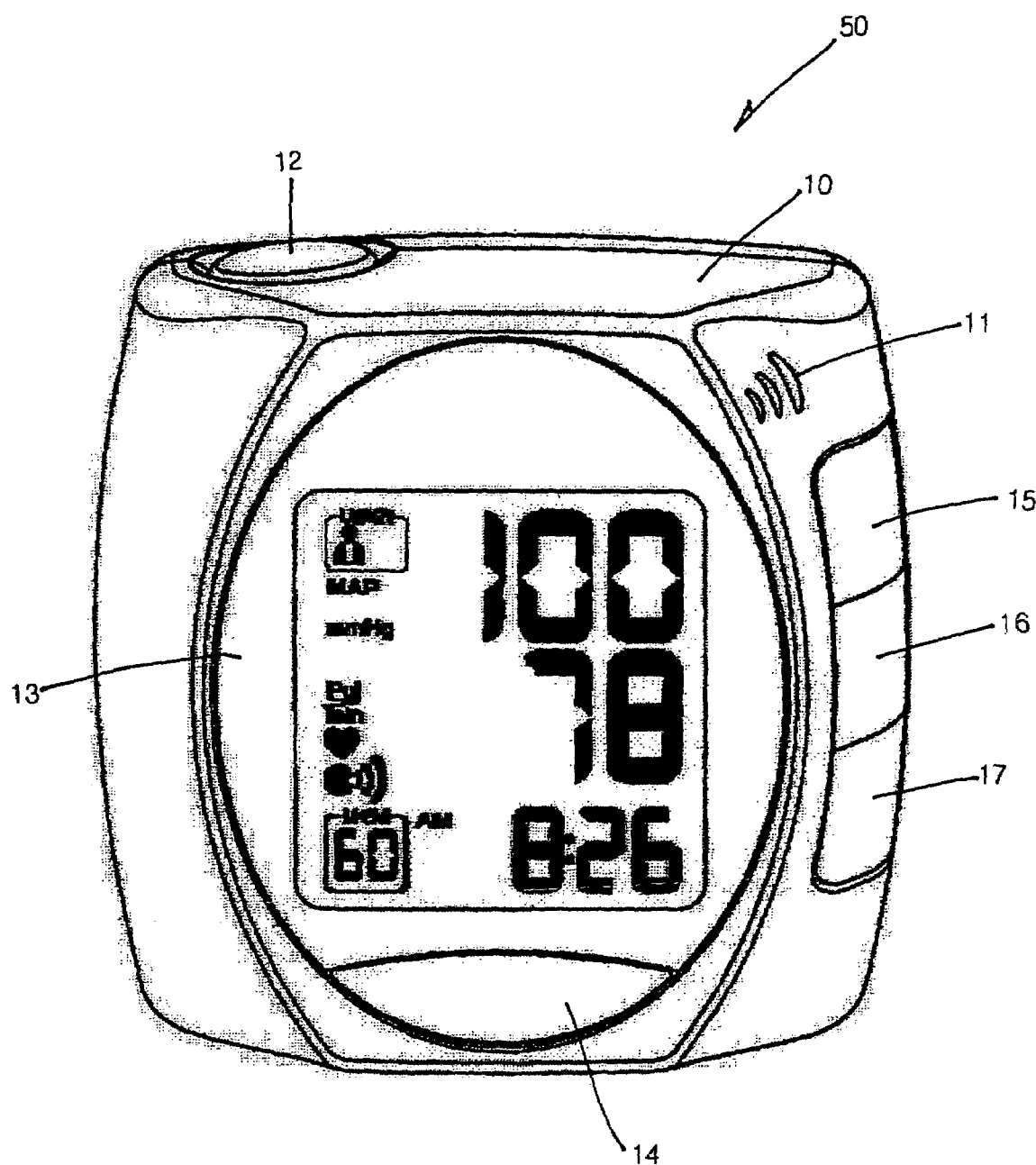
FIG. 1 is a perspective view of an embodiment of a portable blood pressure measuring device in accordance with the invention.

Referring initially to FIG. 1 of the drawings, there is shown a blood pressure measuring device 50 embodying the invention, of the wrist-mounted type, which has a casing 10 and a speaker 11 mounted within the casing 10. There is a talking/volume control key 12 provided at the top side of the casing 10. A liquid crystal display (LCD) panel 13 displays systolic and diastolic blood pressure readings, the time and various other graphic or alphanumeric data/information. There are also a start key 14, a number of say two user keys 15 and 16 for different users, and a set key 17 as depicted. Battery cells (not shown) are installed in the casing 10 for power.

Figure 2:
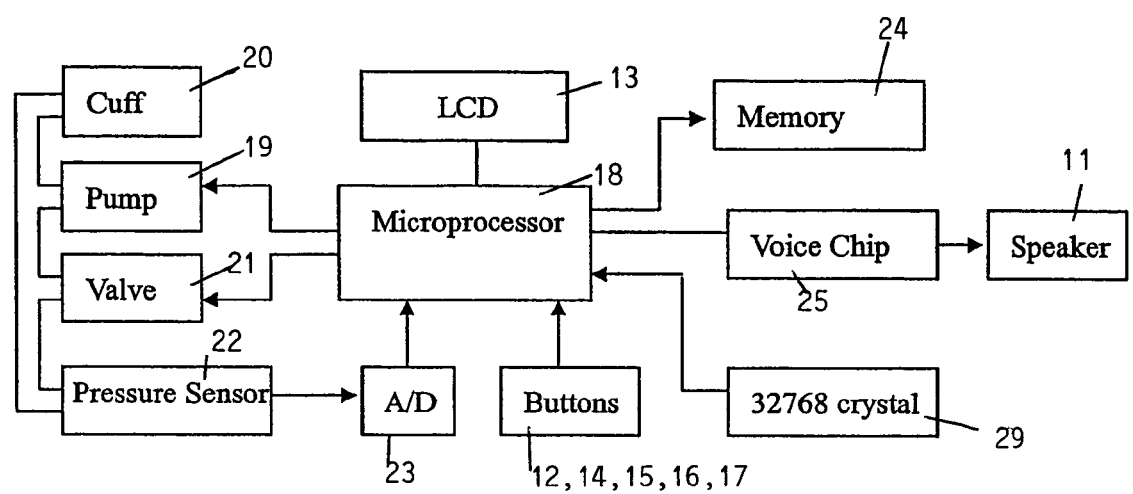
FIG. 2 is a schematic block diagram of the measuring device of FIG. 1, showing its key components.

With reference to FIG. 2, there is provided within the casing 10 a microprocessor 18 for operation and control, including receiving user signals from the keys 12, 14, 15, 16 and 17. Also located within the casing 10 is an electric pump 19 for operation under the control of the microprocessor 18 to inflate a cuff 20. The cuff 20 is built-in or attached directly to the casing 10, designed for use around a user's wrist. There is a pressure relief valve 21 controlled by the microprocessor 18 to open and close as required. The valve 21 is connected pneumatically with the pump 19 as well as a pressure sensor 22 which is in turn connected pneumatically to the cuff 20.

A voice processor chip 25 is connected to the microprocessor 18 and controlled thereby to generate various voice signals according to or based on data received from or via the microprocessor 18. In operation, the voice chip 25 converts such data into electrical sound signals which are in turn amplified to drive the speaker 11 and/or to reach a phone jack (not shown).

An analogue-to-digital or A/D converter 23 receives analogue signals from the pressure sensor 22 and converts them into digital form and then delivers the digital data to the microprocessor 18. A 32768 crystal 29 provides the microprocessor 18 with a clock frequency to perform various time-keeping/clock functions for example to display the time and provide daily alarms, and certain other functions for example in calculating the heart/pulse rate of a user.

There is a solid-state memory 24 (e.g. RAM and EEPROM) connected to the microprocessor 18 for storing data, including data from the microprocessor 18 relating to previous measurement of blood pressure saved against the time (including date) of measurement i.e. the user's records. These records/data will be retrieved by the microprocessor 18 for certain functions or analysis or for display on the LCD panel 13 and/or announcement by the speaker 11.

The voice chip 25 incorporates built-in memory which is pre-loaded with certain types of data primarily for vocal functions, including segments of dialogue for announcing blood pressure, pulse rate and time and a user guide to blood pressure measurement. The microprocessor 18 includes built-in memory that is pre-loaded with a set of blood pressure classifications.

To operate the subject blood pressure measuring device 50, a user should first press the appropriate user key 15/16 to identify himself/herself for correct operation and record processing. Upon pressing of the start key 14, the microprocessor 18 will activate the pump 19 to pressurise and inflate the cuff 20 and then the valve 21 will come in action gradually reducing the pressure in the cuff 20, during which period of time the pressure sensor 22 senses small oscillations in the cuff pressure (as caused by cyclic expansion of the brachial artery) Data relating to the oscillations in pressure is converted by the A/D converter 23 for processing by the microprocessor 18 to calculate and determine the systolic and diastolic pressure values.

At the start of blood pressure measurement, for example upon pressing of the start key 14, under the control of the microprocessor 18 and voice chip 25, the speaker 11 will announce appropriate voice guidance to guide a user to prepare for the measurement. Such voice guidance is based on or select from the aforesaid user guide stored in the voice chip memory, such as "Be seated and rest your forearm at the heart level", "Apply the cuff to your upper arm and press your User key when ready" and later "Please do no speak or move during measurement", etc. These precautions are needed to ensure accurate measurement, and are announced as if a nurse or a professional medical doctor were present.

The measured blood pressure readings will be displayed on the LCD panel 13. Simultaneously or shortly afterward, under the control of the microprocessor 18, the voice chip 25 will generate a voice signal, which incorporates a suitable dialogue segment retrieved from the voice chip memory, such as "Your systolic and diastolic blood pressures are . . . ", for driving the speaker 11 to announce the readings. The vocal announcement function is preferably performed each time after blood pressure is measured, or it may be disabled as desired. There may be a follow-up message (or alert) which is subsequently announced as appropriate.

Figure 4:
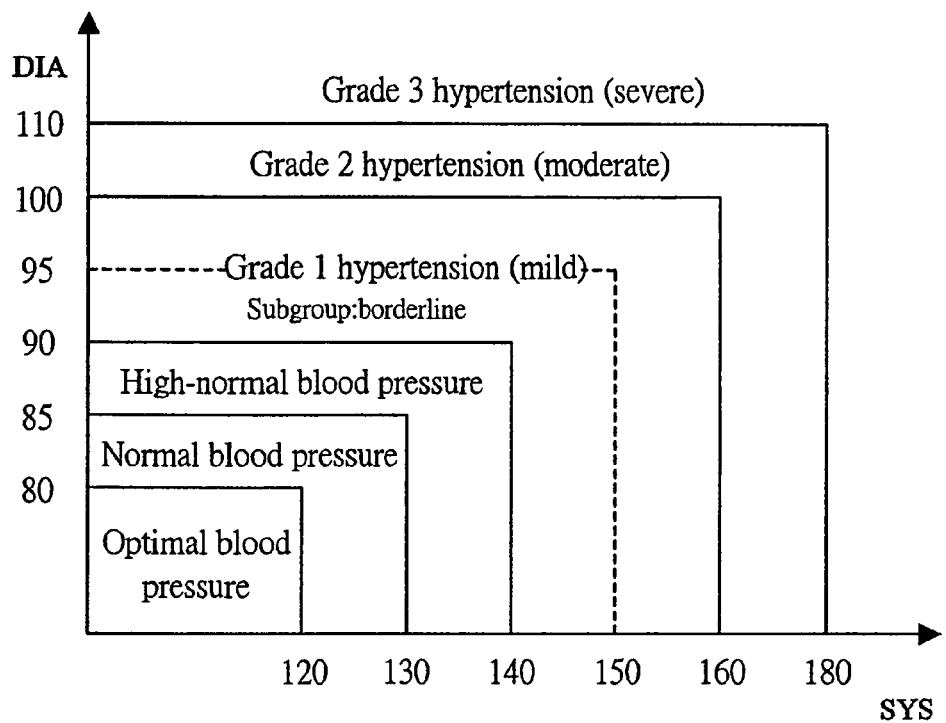
FIG. 4 is reference material from the World Health Organisation—International Society of Hypertension Guidelines for the Management of Hypertension, Journal of Hypertension, 1999, 17(2): 151–183.

An example of such follow-up messages relates to classification of the blood pressure measurement according to the aforesaid blood pressure classifications. The set of classifications is preferably derived from or based on Journal of Hypertension, 1999, 17(2): 151–183 published by the International Society of Hypertension, Guidelines for the Management of Hypertension, of the World Health Organisation, as depicted in FIG. 4.

In operation, the speaker 11 is controlled by the microprocessor 18 and voice chip 25 to announce a voice message to indicate a suitable classification, selected from the set of classifications stored in the microprocessor's internal memory, which corresponds to the measured blood pressure, such as "Your blood pressure is normal" or "Your blood pressure is mildly high, borderline".

The user may need to check his/her blood pressure daily under identical or near identical circumstances. To this end, the user can make use of the clock function in the microprocessor 18 to set a daily alarm at the optimal time of the day for taking measurement. The daily alarm can be set to signal the user by voice, for example "It is now time to check your blood pressure". The daily (voice) alarm may be set manually by the user, or it may be set automatically by the microprocessor 18 following the operation as illustrated in FIG. 3.

Figure 3:
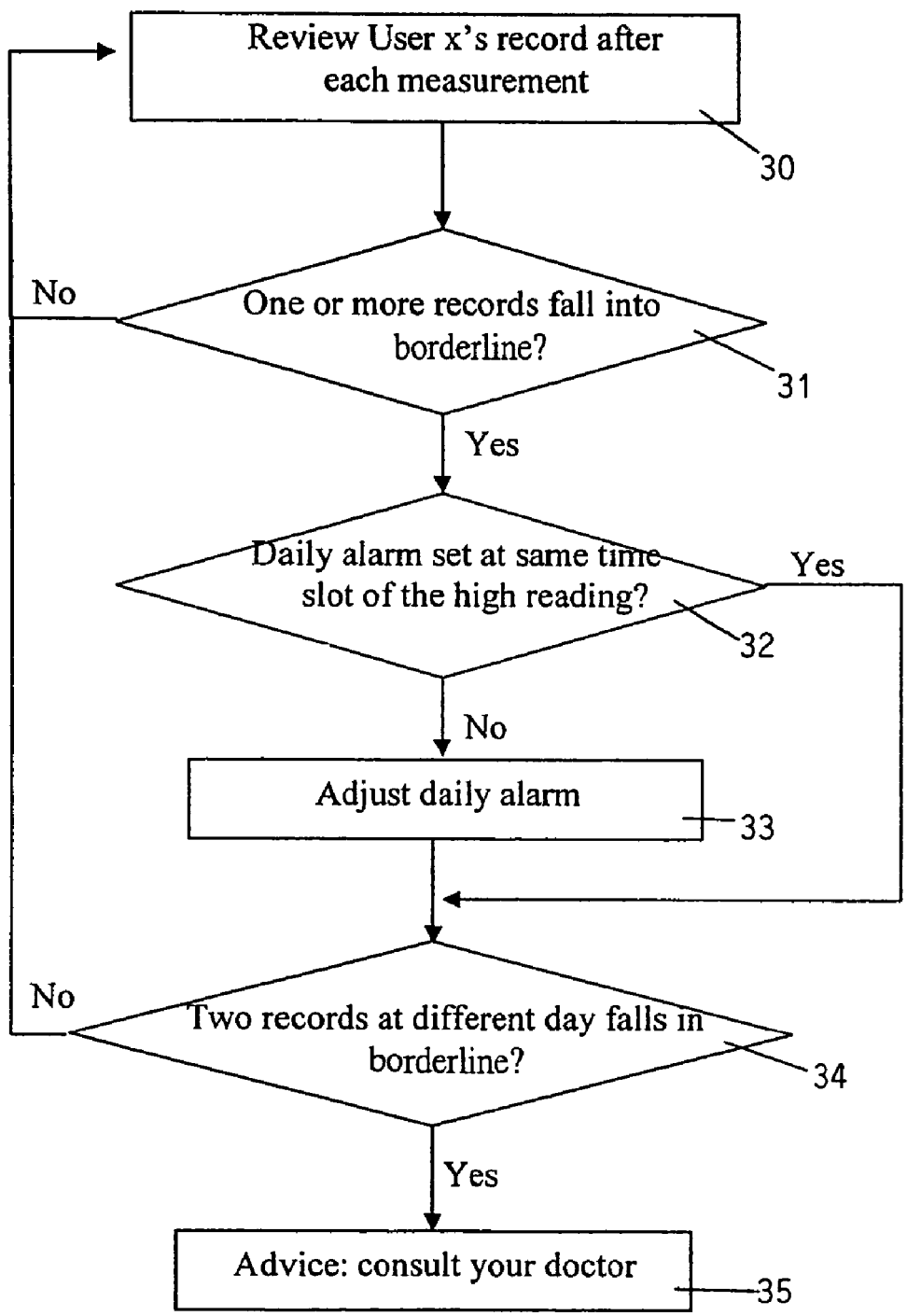
FIG. 3 is a schematic flowchart illustrating memory management and alarm setting and advice for the measuring device of FIG. 1.

In FIG. 3 concerning memory management and alarm setting and advice, upon the microprocessor 18 reviewing or analysing the user's records in the memory 24 after each measurement (step 30), if one or more records are borderline i.e. mildly high (step 31), the daily alarm is automatically set at or adjusted to the same time slot of the high readings (step 32 or 33). If the microprocessor 18 identifies occurrence of borderline or high blood pressure twice within a predetermined period, such as in different days within a week (step 34), it will invoke the voice chip 25 and speaker 11 to announce an alert message, such as "You should consult your doctor" to recommend medical attention (step 35).

The blood pressure measuring device 50 as described above including the built-in voice guidance instructions and voice readout, is convenient to use and is particularly useful for elderly and blind people. The measuring device 50 can be used by more than one user, in that with the use of said at least two user keys 15 and 16 different users can recall their own past measurements (blood pressure data with time stamp) from the memory 24 and take and store new measurements.

The invention has been given by way of example only, and various modifications of and/or alterations to the described embodiment may be made by persons skilled in the art without departing from the scope of the invention as specified in the appended claims. For example, the cuff 20 may be connected by means of a flexible tube to the casing 10 (and the pump 19) and is designed for use around the upper arm of a user.

What is claimed is:

1. A portable blood pressure measuring device comprising:
    a casing;
    a pressure sensor for sensing oscillations in pressure from a cuff, when the cuff is attached to a user;
    a microprocessor provided in the casing for determining blood pressure based on the oscillations in pressure sensed by the pressure sensor;
    a signal converter provided in the casing for operatively converting data from the pressure sensor into data for processing by the microprocessor;
    a voice processor provided in the casing, receiving data from the microprocessor and generating a voice signal indicative of blood pressure determined by the microprocessor;
    time-keeping means associated with the microprocessor for time keeping and providing the time and a daily alarm; and
    memory means connected to the microprocessor for operatively storing values of blood pressure determined by the microprocessor against time of measurement, wherein the microprocessor is programmed to determine an optimal time of the day for blood pressure measurement, based on the blood pressure values against time stored in the memory means, and to indicate the optimal time.

2. The measuring device as claimed in claim 1, wherein the time-keeping means is controlled by the microprocessor to provide a daily alarm at the optimal time.

3. The measuring device as claimed in claim 2, wherein the voice processor is controlled by the microprocessor to generate a voice signal at the optimal time according to the time-keeping means, acting as the daily alarm.

4. The measuring device as claimed in claim 1, wherein the microprocessor is programmed to identify, from the blood pressure values against time stored in the memory means, occurrence of borderline or high blood pressure twice within a predetermined period and then to provide an alert signal.

5. The measuring device as claimed in claim 4, wherein the microprocessor provides the alert signal by controlling the voice processor to generate a voice signal recommending medical attention.

\* \* \* \* \*